(12) United States Patent
Husain et al.

(10) Patent No.: US 9,388,440 B2
(45) Date of Patent: Jul. 12, 2016

(54) ENZYMATIC PROCESS FOR THE PREPARATION OF (S)-5-(4-FLUORO-PHENYL)-5-HYDROXY-1MORPHOLIN-4-YL-PENTAN-1-ONE, AN INTERMEDIATE OF EZETIMIBE AND FURTHER CONVERSION TO EZETIMIBE

(75) Inventors: Mofazzal Husain, Hyderabad (IN); Sarat Chandra Srikanth Gorantla, Hyderabad (IN); Swapna Thorpunuri, Hyderabad (IN); Datta Debashish, Hyderabad (IN)

(73) Assignee: Mylan Laboratories Limited, Hyderabad (IN)

( * ) Notice: Subject to any disclaimer, the term of this patent is extended or adjusted under 35 U.S.C. 154(b) by 415 days.

(21) Appl. No.: 13/262,722

(22) PCT Filed: Mar. 30, 2010

(86) PCT No.: PCT/IN2010/000203
§ 371 (c)(1),
(2), (4) Date: Oct. 3, 2011

(87) PCT Pub. No.: WO2010/113175
PCT Pub. Date: Oct. 7, 2010

(65) Prior Publication Data
US 2012/0028316 A1    Feb. 2, 2012

(30) Foreign Application Priority Data

Apr. 1, 2009  (IN) .............................. 760/CHE/2009
Aug. 21, 2009 (IN) .......................... 1994/CHE/2009
Oct. 14, 2009 (IN) .......................... 2502/CHE/2009

(51) Int. Cl.
C12P 17/14    (2006.01)
C07D 263/26   (2006.01)
C12N 9/20     (2006.01)
C12P 17/10    (2006.01)

(52) U.S. Cl.
CPC ............... *C12P 17/14* (2013.01); *C12P 17/10* (2013.01); *C12N 9/20* (2013.01)

(58) Field of Classification Search
CPC ........... C12P 17/14; C12P 17/10; C12N 9/20; C12Y 101/01184
USPC ............... 435/120, 198, 121, 189, 190
See application file for complete search history.

(56) References Cited

U.S. PATENT DOCUMENTS

| | | |
|---|---|---|
| 4,293,496 A | 10/1981 | Willard |
| 4,444,784 A | 4/1984 | Hoffman et al. |
| 4,450,171 A | 5/1984 | Hoffman et al. |
| 5,618,707 A | 4/1997 | Homann et al. |
| 5,635,365 A | 6/1997 | Ansari et al. |
| 5,728,827 A | 3/1998 | Thiruvengadam et al. |
| 5,739,321 A | 4/1998 | Wu et al. |
| 5,767,115 A | 6/1998 | Rosenblum et al. |
| 5,846,966 A | 12/1998 | Rosenblum et al. |
| 5,856,473 A | 1/1999 | Shankar |
| 5,886,171 A | 3/1999 | Wu et al. |
| 5,919,672 A | 7/1999 | Homann et al. |
| 5,969,156 A | 10/1999 | Briggs et al. |
| 6,096,883 A | 8/2000 | Wu et al. |
| 6,133,001 A | 10/2000 | Homann et al. |
| 6,207,822 B1 | 3/2001 | Thiruvengadam et al. |
| RE37,721 E | 5/2002 | Rosenblum et al. |
| 6,541,640 B2 | 4/2003 | Pazenok et al. |
| 6,627,757 B2 | 9/2003 | Fu et al. |
| 6,864,385 B2 | 3/2005 | Pazenok et al. |
| 6,982,251 B2 | 1/2006 | Ghosal et al. |
| 6,992,067 B2 | 1/2006 | Glombik et al. |
| 7,002,008 B2 | 2/2006 | Framroze |
| 7,030,106 B2 | 4/2006 | Cho |
| 7,053,080 B2 | 5/2006 | Davis et al. |
| 7,056,906 B2 | 6/2006 | Strony |
| 7,067,675 B2 | 6/2006 | Reddy et al. |
| 7,071,181 B2 | 7/2006 | Davis et al. |
| 7,176,193 B2 | 2/2007 | Jaehne et al. |
| 7,388,004 B2 | 6/2008 | Jaehne et al. |
| 7,488,818 B2 | 2/2009 | Lindenschmidt et al. |

(Continued)

FOREIGN PATENT DOCUMENTS

EP    0304208 B1    5/1993
EP    2213638 A1    8/2010

(Continued)

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
International Search Report for WO2010/113175, dated Feb. 25, 2011 (6 pages).

(Continued)

*Primary Examiner* — Tekchand Saidha
*Assistant Examiner* — Md. Younus Meah

(57) ABSTRACT

The present invention provides an enzymatic process for the preparation of (S)-5-(4-Fluoro-phenyl)-5-hydroxy-1morpholin-4-yl-pentan-1-one by the reduction of 1-(4-Fluorophenyl)-5-morpholin-4-yl-pentane-1,5-dione by using a suitable enzyme or by the resolution of (R,S)-5-(4-Fluorophenyl)-5-hydroxy-1morpholin-4-yl-pentan-1-one by using an enzyme. The present invention also provides process for the preparation of Ezetimibe comprising the steps of a) protecting the compound (S)-5-(4-Fluoro-phenyl)-5-hydroxy-1morpholin-4-yl-pentan-1-one with hydroxy protecting group b) hydrolyzing the obtained compound c) condensing with a chiral auxiliary d) reacting with an protected imine compound e) converting to alkyl ester f) cyclizing and g) deprotecting to obtain Ezetimibe.

11 Claims, No Drawings

(56) References Cited

U.S. PATENT DOCUMENTS

| | | |
|---|---|---|
| 7,488,829 B2 | 2/2009 | Glombik et al. |
| 7,498,431 B2 | 3/2009 | Framroze |
| 7,563,888 B2 | 7/2009 | Jendralla et al. |
| 7,576,200 B2 | 8/2009 | Glombik et al. |
| 7,612,058 B2 | 11/2009 | Cho |
| 7,674,773 B2 | 3/2010 | Glombik et al. |
| RE42,461 E | 6/2011 | Rosenblum et al. |
| 2002/0137690 A1 | 9/2002 | Ghosal et al. |
| 2002/0147184 A1 | 10/2002 | Kosoglou et al. |
| 2002/0151536 A1 | 10/2002 | Davis et al. |
| 2002/0183305 A1 | 12/2002 | Davis et al. |
| 2003/0004335 A1 | 1/2003 | Ceresiat et al. |
| 2003/0053981 A1 | 3/2003 | Davis et al. |
| 2003/0069221 A1 | 4/2003 | Kosoglou et al. |
| 2003/0119757 A1 | 6/2003 | Davis |
| 2003/0204096 A1 | 10/2003 | Fu et al. |
| 2004/0097482 A1 | 5/2004 | Davis et al. |
| 2005/0070519 A1 | 3/2005 | Schofield et al. |
| 2005/0171080 A1 | 8/2005 | Sundaram et al. |
| 2005/0250961 A1 | 11/2005 | Pulla |
| 2006/0009399 A1 | 1/2006 | Davis et al. |
| 2006/0135755 A1 | 6/2006 | Thiruvengadam et al. |
| 2006/0160785 A1 | 7/2006 | Aronhime et al. |
| 2006/0199793 A1 | 9/2006 | Cho et al. |
| 2006/0234996 A1 | 10/2006 | Adin et al. |
| 2007/0049748 A1 | 3/2007 | Uppala et al. |
| 2007/0259845 A1 | 11/2007 | Kansal et al. |
| 2008/0032964 A1 | 2/2008 | Kansal et al. |
| 2008/0058305 A1 | 3/2008 | Kansal et al. |
| 2008/0058306 A1 | 3/2008 | Davis et al. |
| 2008/0261942 A1 | 10/2008 | Davis et al. |
| 2009/0047716 A1 | 2/2009 | Perlman et al. |
| 2009/0062527 A1 | 3/2009 | Tomiyama et al. |
| 2009/0227786 A1 | 9/2009 | Escude et al. |

FOREIGN PATENT DOCUMENTS

| | | | |
|---|---|---|---|
| WO | 0034240 | A1 | 6/2000 |
| WO | 0060107 | A1 | 10/2000 |
| WO | 2004099132 | A2 | 11/2004 |
| WO | 2005009955 | A1 | 2/2005 |
| WO | 2005066120 | A2 | 7/2005 |
| WO | 2006050634 | A1 | 5/2006 |
| WO | 2006137080 | A1 | 12/2006 |
| WO | 2007017705 | A1 | 2/2007 |
| WO | 2007072088 | A1 | 6/2007 |
| WO | 2007108007 | A1 | 9/2007 |
| WO | 2007144780 | A2 | 12/2007 |
| WO | 2008032338 | A2 | 3/2008 |
| WO | 2008089984 | A2 | 7/2008 |
| WO | 2008096372 | A2 | 8/2008 |
| WO | 2008106900 | A1 | 9/2008 |
| WO | 2008108145 | A1 | 9/2008 |
| WO | 2008151324 | A1 | 12/2008 |
| WO | 2009032264 | A1 | 3/2009 |
| WO | 2009052246 | A1 | 4/2009 |
| WO | 2009052248 | A1 | 4/2009 |
| WO | 2009054887 | A1 | 4/2009 |
| WO | 2009067960 | A2 | 6/2009 |
| WO | 2009077573 | A2 | 6/2009 |
| WO | 2009106021 | A1 | 9/2009 |
| WO | 2009140932 | A2 | 11/2009 |
| WO | 2009150038 | A1 | 12/2009 |
| WO | 2009157019 | A2 | 12/2009 |
| WO | 2010006954 | A1 | 1/2010 |
| WO | 2010010579 | A1 | 1/2010 |
| WO | 2010012775 | A1 | 2/2010 |
| WO | 2010025085 | A2 | 3/2010 |
| WO | 2010071358 | A2 | 6/2010 |
| WO | 2010097350 | A1 | 9/2010 |
| WO | 2010112222 | A1 | 10/2010 |
| WO | 2010113182 | A1 | 10/2010 |
| WO | 2010113184 | A1 | 10/2010 |
| WO | 2010141494 | A2 | 12/2010 |
| WO | 2010144066 | A1 | 12/2010 |
| WO | 2011000212 | A1 | 1/2011 |

OTHER PUBLICATIONS

Written Opinion of the International Searching Authority for WO2010/113175 (8 pages).

Kaluzna et al, "Ketoreductases: stereoselective catalysis for the facile synthesis of chiral alcohols" Tetrahedron Asymmetry, vol. 16, No. 22, Nov. 14, 2005, pp. 3682-89.

Xu, C et al., "Candida Rugosa lipase-catalyzed kinetic resolution of beta-hydroxy-beta-arylpropionates and delta-hydroxy-delta-arayl-beta-oxo-pentanoates" Tetrahedron, vol. 61, No. 8, Feb. 21, 2005, pp. 2169-86.

Nair, M.S. et al., "Lipase catalyzed kinetic resolution of aryl beta-hydroxy ketones" Tetrahedron Asymmetry, vol. 11, No. 10, Jun. 1, 2000, pp. 2049-52.

* cited by examiner

ENZYMATIC PROCESS FOR THE PREPARATION OF (S)-5-(4-FLUORO-PHENYL)-5-HYDROXY-1MORPHOLIN-4-YL-PENTAN-1-ONE, AN INTERMEDIATE OF EZETIMIBE AND FURTHER CONVERSION TO EZETIMIBE

This application claims priority to Indian patent application No.'s 760/CHE/2009 filed on Apr. 1, 2009, 1994/CHE/2009 filed on Aug. 21, 2009 and 2502/CHE/2009 filed on Oct. 14, 2009, the contents of which are incorporated by reference in their entirety

FIELD OF THE INVENTION

The present invention relates to an enzymatic process for the preparation of (S)-5-(4-Fluoro-phenyl)-5-hydroxy-1-morpholin-4-yl-pentan-1-one, and its further conversion to Ezetimibe.

BACKGROUND OF THE INVENTION (3R,4S)-1-(4-Fluorophenyl)-3-[3(S)-3-(4-fluorophenyl)-3-hydroxypropyl)]-4-(4-hydroxyphenyl)-2-azetidinone (Ezetimibe) represented by formula I, is an useful hypocholesterolemic agent.

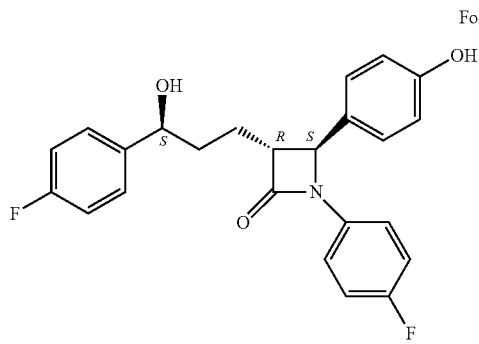

Formula I

Ezetimibe is a lipid-lowering compound in the class of azetidinones that selectively inhibits the intestinal absorption of cholesterol and related phytosterols. Ezetimibe is sold under the commercial name Zetia®.

U.S. Pat. No. 6,096,883 discloses generically and specifically ezetimibe and its related compounds along with their pharmaceutical compositions. The patent also describes a process for the preparation of ezetimibe The process for the preparation of ezetimibe was disclosed in U.S. Pat. Nos. 5,631,365; 5,739,321; 5,856,473; 5,767,115 and 6,207,822. The prior art process used chiral auxiliary for the preparation of Ezetimibe. However, there are several drawbacks associated with the processes describe in the art. These drawbacks include the use of pyrophoric bases, such as n-butyl lithium and a metalamide, e.g., LDA, and low temperatures, e.g., below −50 degree. C., which lead to difficulties in preparation of ezetimibe on a commercial scale.

WO 20080151324 and US 2009/0047716 disclosed the reduction process for the preparation of ezetimibe using ketoreductase enzymes. The reduction of EZT-Ketone is done in the presence of a co-factor and buffer.

Accordingly, there remains a need for improved processes for preparing ezetimibe that eliminates and reduces the drawbacks of the prior art in a convenient and cost efficient manner on a commercial scale. The process according to the present invention relates to an enzymatic process for the preparation of the hydroxyl intermediate of ezetimibe. The enzymatic reduction process of the present invention is eco-friendly, cost effective and commercially viable. The present invention involves the recovery of chiral auxiliary which is cost effective.

OBJECT AND SUMMARY OF THE INVENTION

The main object of the present invention is to provide, an enzymatic process for the preparation of (S)-5-(4-Fluoro-phenyl)-5-hydroxy-1morpholin-4-yl-pentan-1-one, and its further conversion to ezetimibe.

One more object of the present invention is to provide, an enzymatic process for the preparation of (S)-5-(4-Fluoro-phenyl)-5-hydroxy-1morpholin-4-yl-pentan-1-one, comprising the steps of: treating 1-(4-Fluoro-phenyl)-5-morpholin-4-yl-pentane-1,5-dione with enzyme selected from ketoreductase family and isolating (S)-5-(4-Fluoro-phenyl)-5-hydroxy-1morpholin-4-yl-pentan-1-one.

Yet one more object of the present invention is to provide, an enzymatic process for the resolution of (R,S) 5-(4-Fluorophenyl)-5-hydroxy-1-morpholin-4-yl-pentane-1-one, comprising the steps: treating (R,S) 5-(4-Fluorophenyl)-5-hydroxy-1-morpholin-4-yl-pentane-1-one with an enzyme selected from Lipases family and isolating (S)-5-(4-Fluoro-phenyl)-5-hydroxy-1morpholin-4-yl-pentan-1-one.

Yet one more object of the present invention is to provide, a novel process for the preparation of ezetimibe via (S)-5-(4-Fluoro-phenyl)-5-hydroxy-1morpholin-4-yl-pentan-1-one.

Yet one more object of the present invention is to provide, pharmaceutical compositions containing ezetimibe, which is prepared according to present invention

DETAIL DESCRIPTION OF THE INVENTION

The present invention provides an enzymatic process for the preparation of (S)-5-(4-Fluoro-phenyl)-5-hydroxy-1morpholin-4-yl-pentan-1-one by the reduction of 1-(4-Fluoro-phenyl)-5-morpholin-4-yl-pentane-1,5-dione by using a suitable enzyme or by the resolution of (R,S)-5-(4-Fluoro-phenyl)-5-hydroxy-1morpholin-4-yl-pentan-1-one by using an enzyme.

The present invention also provides process for the preparation of Ezetimibe comprising the steps of a) protecting the compound (S)-5-(4-Fluoro-phenyl)-5-hydroxy-1morpholin-4-yl-pentan-1-one with hydroxy protecting group b) hydrolyzing the obtained compound c) condensing with a chiral auxiliary d) reacting with an protected imine compound e) converting to alkyl ester f) cyclizing and g) deprotecting to obtain Ezetimibe.

Accordingly the present invention provides an enzymatic process for the preparation of (S)-5-(4-Fluoro-phenyl)-5-hydroxy-1morpholin-4-yl-pentan-1-one as summarized in scheme I

SCHEME I

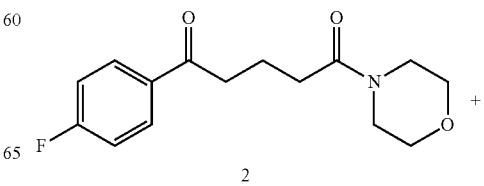

2

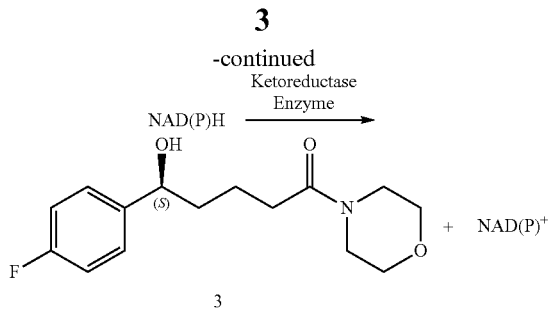

Asymmetric reduction of 1-(4-Fluoro-phenyl)-5-morpholin-4-yl-pentane-1,5-dione using enzymes such as ES-KRED-106 or ES-KRED-119 in the presence of a buffer to give (S)-5-(4-Fluoro-phenyl)-5-hydroxy-1morpholin-4-yl-pentan-1-one The "KRED" or ketoreductase enzyme used in the present invention refers to an enzyme that catalyzes the reduction of a ketone to form the corresponding alcohol. Ketoreductase enzymes include, for example, those classified under the Enzyme Commission ("EC") numbers of 1.1.1. Such enzymes are given various names in addition to ketoreductase, including, but not limited to, alcohol dehydrogenase, carbonyl reductase, lactate dehydrogenase, hydroxyacid dehydrogenase, hydroxyisocaproate dehydrogenase, β-hydroxybutyrate dehydrogenase, steroid dehydrogenase, sorbitol dehydrogenase, aldoreductase, and the like. NADPH-dependent ketoreductases are classified under the EC number of 1.1.1.2 and the CAS number of 9028-12-0. NADH-dependent ketoreductases are classified under the EC number of 1.1.1.1 and the CAS number of 9031-72-5. Ketoreductases are commercially available, for example, from Chiral Vision/Enzysource under the catalog numbers ES-KRED-101 to ES-KRED-162.

Suitable ketoreductases include, but are not limited to, Syncore Laboratories products with catalog numbers ES-KRED-104, ES-KRED-105, ES-KRED-106, ES-KRED-107, ES-KRED-115, ES-KRED-117, ES-KRED-118, ES-KRED-119, ES-KRED-120, ES-KRED-121, ES-KRED-125, ES-KRED-128, ES-KRED-133, ES-KRED-142, equivalent products thereof, and mixtures thereof; As used herein, the term "equivalent" refers to an enzyme or product with similar or identical enzymatic activity. More preferably, the ketoreductase is selected from the group consisting of the predominant enzyme in each of ES-KRED-106, ES-KRED-119, and mixtures thereof.

According to the present invention, reduction of compound of formula 2 uses a co-factor with the ketoreductase enzyme. The co-factor is selected from the group consisting of NADH, NADPH, NAD$^+$, NADP$^+$, salts thereof or analogs thereof.

According to the present invention, reduction of compound of formula 2 comprises a co-factor regeneration system. A co-factor regeneration system comprises a substrate and a "dehydrogenase enzymes". Preferably, the co-factor regeneration system comprises a substrate/dehydrogenase pair selected from the group consisting of D-glucose/glucose dehydrogenase, sodium formate/formate dehydrogenase, and phosphite/phosphite dehydrogenase. Glucose dehydrogenase (GDH) includes, for example, those classified under the EC number 1.1.1.47 and the CAS number 9028-53-9, and are commercially available, for example, from Syncore Laboratories under the catalog number ES-GDH-101 to ES-GDH-104 or Codexis, Inc. under the catalog number GDH-CDX-901. Preferably, the glucose dehydrogenase is selected from the group consisting of the predominant enzyme in each of Syncore Laboratories products with catalog numbers ES-GDH-101, ES-GDH-102, ES-GDH-103, ES-GDH-104 and Codexis Inc's products with catalog numbers GDH-CDX901, and mixtures thereof.

According to the present invention, reduction of compound of formula 2, comprises adding a solvent. Preferably, the solvent is water-miscible organic solvent which is selected from the group consisting of alcohol and DMSO. Preferably, the alcohol is a $C_1$-$C_6$ alcohol, more preferably methanol or IPA. The advantage of the preferred solvents used in this process, compared to the organic solvents used in prior art reference, is that their medium is mostly water, which makes the reaction more environmentally friendly.

According to the present invention, reduction of compound of formula 2, is carried out in a buffer having a pH selected from 4 to 9. Preferably, the buffer is a solution of salt. Preferably, the salt is potassium phosphate, and mixtures thereof.

According to the present invention, reduction of compound of formula 2, is carried out at a temperature of about 10° C. to about 50° C.

As per the present invention, the ketoreductase enzyme is dissolved in buffer and to this a solution of 1-(4-Fluoro-phenyl)-5-morpholin-4-yl-pentane-1,5-dione in an alcohol solvent such as methanol is added at a temperature of 20-40° C. for 15-40 hours and monitored by HPLC. To this immiscible organic solvent such as ethyl acetate is added and (S)-5-(4-Fluoro-phenyl)-5-hydroxy-1morpholin-4-yl-pentan-1-one is isolated from organic phase.

In one aspect, the present invention relates to an enzymatic process for the resolution of (R,S) 5-(4-Fluorophenyl)-5-hydroxy-1-morpholin-4-yl-pentane-1-one, an intermediate of ezetimibe.

In one embodiment, the present invention relates to an enzymatic process for the resolution of (R,S) 5-(4-Fluorophenyl)-5-hydroxy-1-morpholin-4-yl-pentane-1-one as summarized in scheme II

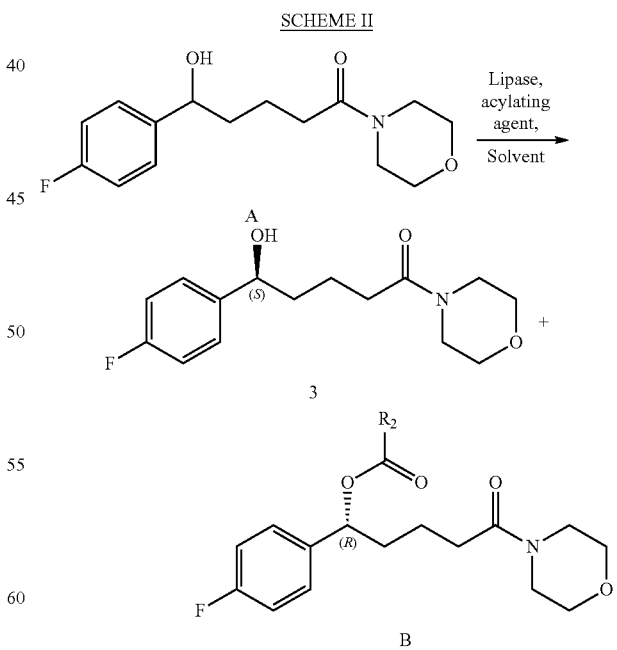

In another embodiment, the resolution process according to the present invention comprising the steps of: dissolving compound of formula A in an appropriate solvent, adding acylating agent, adding enzyme, removing the solvent and isolating the compound of formula 3. The compound of formula B wherein $R_2$ can be methyl, ethyl, propyl, butyl, phenyl, benzyl or $CH_2CH_2COOH$, is isolated from the resultant solution by adjusting the pH using 1N HCl, extracting with suitable organic solvent such as methylene dichloride, removing the solvent and isolating the compound of formula B.

According to the present invention, the solvent used for the resolution of compound of formula A is selected from toluene, hexane, cyclohexane, heptane, dimethylformamide, dichloromethane and their mixtures thereof According to the present invention, the acylating agent used for the resolution of compound of formula A is selected from vinyl acetate, vinyl propionate, isopropenyl acetate, succinic anhydride, acetic anhydride, and the like.

According to the present invention, the Lipase enzyme used for the resolution of compound of formula A is selected from Porcine Pancreatic Lipase, *Candida antartica* lipase A (CAL-A), lyophilized *Candida lipolytica* Lipase, *Geotrichum candidum* Lipase, *Pseudomonas aroginosa* Lipase, *Aspergillus niger* Lipase, *Pseudomonas fluorescens* Lipase, *Candida rugosa* Lipase, *Rhizopus delemar* Lipase, *Rhizopus oryzae* Lipase, *Penicillium camembertii* Lipase, *Penicillium camembertii* Lipase, *Mucor javanicus* Lipase, *Penicillium roqueforti* Lipase, *Pseudomonas cepacia* Lipase, PSC D-1, *Candida antartica* lipase B (CAL-B), lyophilized microbial, lyophilized Lipase, *Thermomyces* sp. Lipase, *Alcaligines* sp., *Chromobacterium viscosum* Lipase, *Candida utilis* Lipase, *Rhizopus niveus* Lipase, *Pseudomonas* sp. Lipoprotein Lipase, *Thermomuces lanuginosus* Lipase, *Rhizomucor miehei* Lipase, *Pseudomonas* species Lipase, Wheat Germ Lipase, *Rhizopus arrhizus* Lipase, Pancreatic Lipase 250, *Candida antartica* lipase B (Novozyme-435), *Candida antartica* lipase A (IMMCALA-T2-150) and the like According to the present invention, resolution of compound of formula A is carried out at a temperature of about 25° C. to about 50° C.

As per the present invention, to the solution of (R,S) 5-(4-Fluorophenyl)-5-hydroxy-1-morpholin-4-yl-pentane-1-one in an organic solvent such as toluene, vinyl acetate and lipase is added and stirred at a temperature of 25° C. to 55° C., preferably at 35° C. to 40° C. and monitored by HPLC. The mixture is filtered and concentrated under reduced pressure to give (S)-5-(4-Fluoro-phenyl)-5-hydroxy-1morpholin-4-yl-pentan-1-one.

The advantages of the present invention are that the Lipases enzyme used in the present invention are cheap thus makes the invention cost effective, avoiding use of chiral axillaries and lower temperatures, performing the reaction in the presence of a solvent at ambient temperature.

In another aspect, the present invention relates to novel process for the preparation of Ezetimibe via (S)-5-(4-Fluorophenyl)-5-hydroxy-1morpholin-4-yl-pentan-1-one an intermediate of Ezetimibe as summarized in scheme III.

SCHEME III

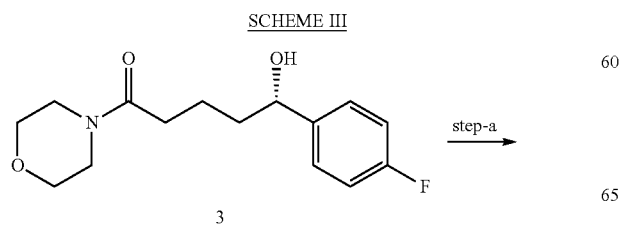

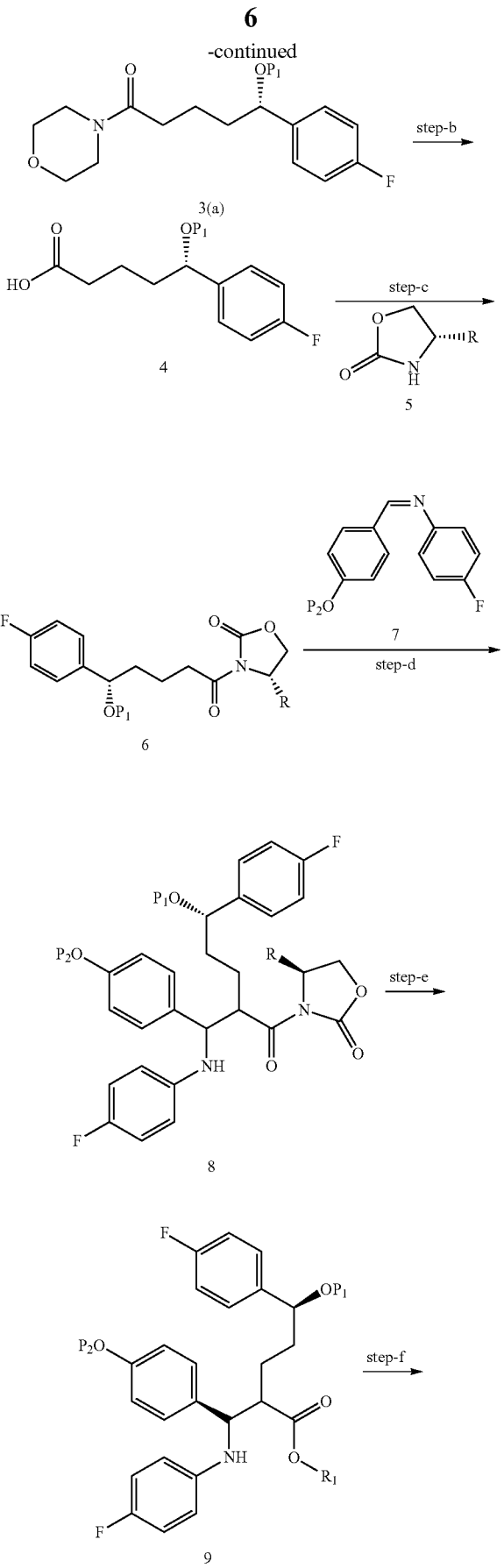

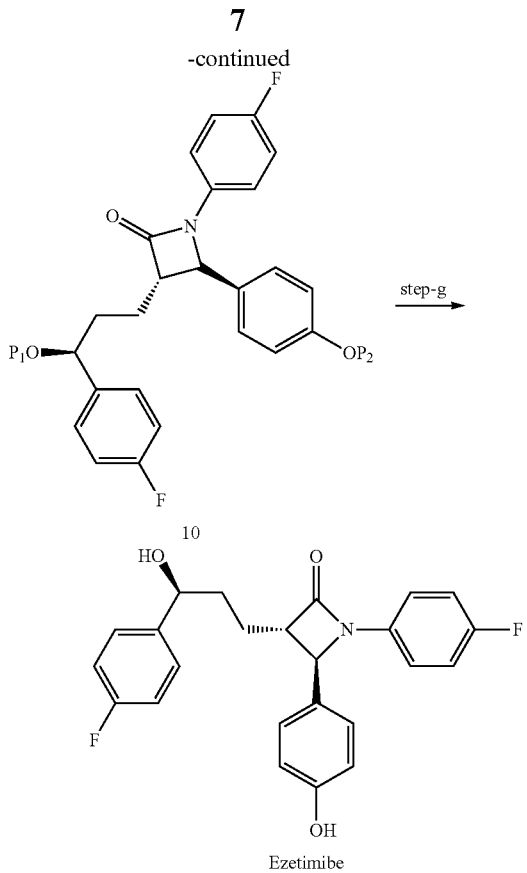

Ezetimibe

In one embodiment, the process for the preparation of Ezetimibe which comprising the steps of:
a) protecting the alcoholic group of compound of formula (3) to produce compound of formula 3(a), wherein $P_1$ is a hydroxy protecting group selected from benzyl or silyl protecting groups.
b) hydrolyzing the compound of formula 3(a) to get compound of formula (4)
c) condensing the compound of formula (4) with Evan's auxiliary of formula (5), wherein R is $C_1$-$C_6$ alkyl, phenyl, naphthyl, substituted phenyl, substituted naphthyl, $C_1$-$C_6$ alkoxycarbonyl or benzyl to get compound of formula (6),
d) reacting the compound of formula (6) with compound of formula (7) wherein $P_2$ is a hydroxy protecting group selected from benzyl or silyl protecting groups with a proviso that one of the $P_1$ and $P_2$ is benzyl protecting group to produce compound of formula (8),
e) converting compound of formula (8) to a compound of formula (9), wherein $R_1$ is $C_1$-$C_6$ alkyl, substituted $C_1$-$C_6$ alkyl, aryl or substituted aryl in presence of base,
f) cyclizing compound of formula (9) to get compound of formula (10), and
g) deprotecting compound of formula (10) to get Ezetimibe.

In one embodiment of the present invention, the compound of formula 3 is protected with a suitable protecting group to obtain compound of formula 3(a), wherein the protecting group is selected from benzyl or silyl protecting groups.

In another embodiment of the present invention, the compound of formula 3(a) is hydrolyzed in presence of alkali metal hydroxides such as sodium hydroxide, potassium hydroxide, preferably potassium hydroxide to obtain compound of formula 4.

In another embodiment of the present invention, the compound of formula 4 is treated with a chiral auxiliary of formula 5 in presence of a base and pivaloyl chloride to obtain a compound of formula 6. The base is selected from trialkylamine such as triethylamine. The chiral auxiliary of the formula 5 is exemplified by the formula:

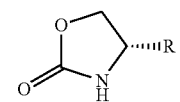

Wherein R is $C_1$-$C_6$ alkyl, phenyl, naphthyl, substituted phenyl, substituted naphthyl, $C_1$-$C_6$ alkoxycarbonyl or benzyl, wherein the substituents on phenyl and naphthyl are 1-3 substituents selected from the group consisting of $C_1$-$C_6$ alkyl, phenyl and benzyl.
The preferred chiral auxiliary is

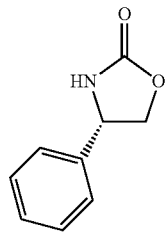 [SMILES: O=C1N[C@@H](c2ccccc2)CO1]

In one more embodiment of the present invention, the compound of formula 6 is condensed with a protected imine compound of formula 7 in a solvent such as chlorinated solvents, aromatic hydrocarbon solvents, preferably dichloromethane in presence of organic amine base like DIPEA and a Lewis acid such as $TiCl_4$ to obtain compound of formula 8. The protecting group used in the compound of formula 7 is selected from benzyl or silyl protecting group with a proviso that one of the $P_1$ and $P_2$ is benzyl protecting group.

In one more embodiment of the present invention, the compound of formula 8 is reacted with a base such as alkalimetal alkoxide or aryloxide in a solvent such as chlorinated solvents, aromatic hydrocarbon solvents, preferably dichloromethane, to obtain alkyl or aryl ester compound of formula 9. Alkalimetal alkoxide used in this reaction is selected from sodium, alkoxide, potassium alkoxide, preferably sodium methoxide. In this step chiral auxiliary is recovered and used for the preparation of compound of formula 6 without purification.

In one more embodiment of the present invention, the alkyl or aryl ester compound of formula 9 is cyclized in the presence of strong non-nucleophilic base such as Sodium bistrimethylsilylamide, Lithium bis(trimethylsilyl)amide or bistrimethyl acetamide along with tetrabutylammonium fluoride, Preferably Lithium bis(trimethylsilyl)amide to obtain the protected azetidinone compound of formula 10.

In yet another embodiment of the present invention, removal of the protecting groups of compound of formula 10 is carried out by conventional methods, for example by the treatment with Pd catalyst in a solvent such as an alcohol like methanol to obtain Ezetimibe.

As per the present invention, the compound of formula 3 is protected with a suitable protecting group to obtain compound of formula 4, wherein the protecting group is selected from benzyl or silyl protecting groups. The obtained compound of formula 4 is treated with chiral auxiliary in presence of trialkylamine such as triethylamine and pivaloyl chloride to obtain compound of formula 6. The compound of formula 6 is condensed with an imine compound of formula 7 in dichloromethane in the presence of DIPEA and $TiCl_a$ to obtain a compound of formula 8. The obtained compound of formula 8 s reacted with sodium alkoxide or aryloxide such as sodium methoxide in presence of dichloromethane to obtain methyl ester compound of formula 9 and it is cyclised in the presence of Lithium bis(trimethylsilyl)amide to obtain compound of formula 10. The compound of formula 10 is treated with Pd catalyst in methanol to give Ezetimibe.

The advantages of the present invention are that the enzymes used in the preparation of Ezetimibe are cheap thus makes the invention cost effective, and the chiral auxiliary used in this process is recovered and again used without purification.

In one more aspect, the present invention relates a pharmaceutical composition that includes a therapeutically effective amount of Ezetimibe prepared according to the processes of the present invention and one or more pharmaceutically acceptable carriers, excipients or diluents.

Accordingly, the pharmaceutical composition comprising Ezetimibe along with one or more pharmaceutically acceptable carriers of this invention may further be formulated as: solid oral dosage forms such as, but not limited to, powders, granules, pellets, tablets, and capsules; liquid oral dosage forms such as but not limited to syrups, suspensions, dispersions, and emulsions, and injectable preparations such as but not limited to solutions, dispersions, and freeze dried compositions. Formulations may be in the form of immediate release, delayed release or modified release. The compositions may be prepared by direct blending, dry granulation, or wet granulation or by extrusion and spheronization. Compositions may be presented as uncoated, film coated, sugar coated, powder coated, enteric coated or modified release coated. Compositions of the present invention may further comprise one or more pharmaceutically acceptable excipients.

The following examples are provided for illustrative purposes only and are not intended to limit the scope of the invention in any way

EXPERIMENTAL PROCEDURE

Starting Material Preparation:

Process for the preparation of 5-(4-Fluoro-phenyl)-5-oxo-pentanoic acid 25 gms of Aluminium chloride was added to 50 ml of dichloromethane and 4.5 ml of fluorobenzene. To this a solution of 50 ml of dichloromethane containing 10 gms of glutaric anhydride and 4.5 ml of fluorobenzene was added. Reaction mass was stirred at room temperature. After completion of reaction, reaction mass was quenched with ice & HCl solution at 0-10° C. Filtered the reaction mass. The obtained wet solid was dissolved in aq $NaHCO_3$ solution at 60-70° C. and insoluable material was filtered. Cooled the filtrate and adjust pH to 2.0 by adding hydrochloric acid. Obtained solid was filtered and dried at 60-70° C. under vacuum to get 10 gm of 5-(4-Fluoro-phenyl)-5-oxo-pentanoic acid.

Process for the preparation of 1-(4-Fluoro-phenyl)-5-morpholin-4-yl-pentane-1,5-dione 10 gms of 5-(4-Fluoro-phenyl)-5-oxo-pentanoic acid and 5.6 gms of triethyl amine was added to 25 ml of toluene. 5.1 gms of Pivollyl chloride was added and stirred the reaction mass at room temperature for about 2 hours. 4 ml of Morpholine in 25 ml of toluene was added to the reaction mass at 0° C. Stirred the reaction mass for about 30 minutes at 0-5° C. and 20 ml of water was added. To the reaction mass 30 ml of brine solution was added and organic layer was separated. Dried the separated organic layer over sodium sulfate. Distill off the solvent completely under reduced pressure at 50-55° C. The resulted oily mass was dissolved in 12 ml of toluene and 60 ml of hexane. Cooled the reaction mass and 12 ml of toluene was added. Stirred the reaction mass for about 1-2 hours at 0-5° C., filtered, washed with 5 ml of hexane and dried at 40-45° C. to get 10 gms of 1-(4-Fluoro-phenyl)-5-morpholin-4-yl-pentane-1,5-dione.

EXAMPLE 1

Reduction of 1-(4-Fluoro-phenyl)-5-morpholin-4-yl-pentane-1,5-dione with ES-KRED-106

ES-KRED-106 (5 mg, Chiral Vision) was dissolved in 5 ml buffer (containing 250 mM potassium phosphate, 5 mg NADP+, 330 mM D-glucose, 2 U/ml glucose dehydrogenase, (GDH) pH 7.0). A solution of 1-(4-Fluoro-phenyl)-5-morpholin-4-yl-pentane-1,5-dione in MeOH (4 mg in 0.2 ml) was added. The mixture was stirred at 31° C. for 24 hrs and monitored by HPLC. Ethyl acetate (5 ml) was added and the phases were separated. The organic layer was evaporated to get the (S)-5-(4-Fluoro-phenyl)-5-hydroxy-1morpholin-4-yl-pentan-1-one. (ee: 90-95%).

EXAMPLE 2

Reduction of 1-(4-Fluoro-phenyl)-5-morpholin-4-yl-pentane-1,5-dione with ES-KRED-119

ES-KRED-119 (3.5 gm, Chiral Vision) was dissolved in 450 ml buffer (containing 250 mM potassium phosphate, 2 gm NADP+, 330 mM D-glucose, 1 gm glucose dehydrogenase, pH 7.0). A solution of 1-(4-Fluoro-phenyl)-5-morpholin-4-yl-pentane-1,5-dione in MeOH (50 gm in 50 ml) was added. The mixture was stirred at 31° C. for 24 hrs and monitored by HPLC. Ethyl acetate (250 ml) was added and the phases were separated. The organic layer was evaporated to get 49 gms of the (S)-5-(4-Fluoro-phenyl)-5-hydroxy-1morpholin-4-yl-pentan-1-one (ee: >99%).

EXAMPLE 3

Process for the preparation of (S)-5-(4-Fluoro-phenyl)-5-hydroxy-1morpholin-4-yl-pentan-1-one To a solution of (R,S)-5-(4-Fluoro-phenyl)-5-hydroxy-1morpholin-4-yl-pentan-1-one (50 g) in toluene (500 mL) vinyl acetate (50 ml, 3 eq) and Candida antartica lipase A (IMMCALA-T2-150) (5 g) were added, and the mixture was stirred by mechanical stirrer at 35 to 40° C. The course of the reaction was followed by HPLC till conversion was around 55 to 57%. The enzyme was filtered and the filtrate was concentrated under reduced pressure. The crude product was purified to give (S)-5-(4-Fluoro-phenyl)-5-hydroxy-1morpholin-4-yl-pentan-1-one (18 g) with ee>99% to 99% and (R)-ester B for ee 70 to 85%.

EXAMPLE 4

Process for the preparation of (S)-5-(4-Fluoro-phenyl)-5-hydroxy-1morpholin-4-yl-pentan-1-one To a solution of (R,S)-alcohol 1 (5 g) in toluene (50-75 mL) were added succinic anhydride (1.75 g) and CAL A (500 mg), and the mixture was stirred at 35 to 45° C. The course of the reaction was followed by HPLC till 43-45% unreacted alcohol and 55 to 57% hemisuccinate was observed. The reaction was stopped by filtering out the enzyme. The filtrate was extracted with 5% NaHCO3 (4×30 mL). The toluene layer was separated from the aqueous layer and dried and evaporated on reduced pressure to get (S)-alcohol 3 (2-2.3 g with 95-99% ee).

To isolate the hemisuccinate ester B, the 5% NaHCO3 layer was adjusted to pH 4-4.5 by slow addition of 1N HCl. After acidification, the aqueous layer was extracted with MDC (3×40 mL). The MDC extract was washed with 10% NaCl (3×20 mL) until the washing was neutral. Removal of MDC gave the hemisuccinate ester B.

EXAMPLE 5

Process for the preparation of (S)-5-(4-Fluoro-phenyl)-5-hydroxy-1morpholin-4-yl-pentan-1-one To a solution of (R,S)-5-(4-Fluoro-phenyl)-5-hydroxy-1morpholin-4-yl-pentan-1-one (750 gm) in toluene (750 ml) vinyl acetate (459 gm) and *Candida antartica* lipase A (IM-MCALA-T2-150) (75 gm) were added and maintained at 36-40° C. for 4-8 hours. The reaction mass was cooled, enzyme was filtered and solvent was distilled under vacuum. To the residue toluene (200 ml), succinic anhydride (133 gm), TEA (215 gm) and DMAP (16 gm) were added and heated the reaction mixture up to 85-90° C. for 4-5 hrs. The reaction mixture was extracted with 5% sodium bicarbonate solution (1.5 Lit) and the aq layer was washed with toluene (1.5 Lit). Again Toluene (0.5 Lit) and NaOH (0.133 Kg) was charged in the aq. layer and stirring the reaction mixture at 25-30° C. for 1-1.5 hrs. Separate the layers and extracted the aq. layer with ethyl acetate (1.0 Lit), combined the organic layer washed with 20% HCl solution followed by washing with 10% NaCl solution. The organic layer was evaporated completely and Heptane was added to the residue and stirred at 25-30 C for 10-12 hrs, filtered the solid and washed with Heptane, dry the solid under vacuum to yield the (S)-5-(4-Fluoro-phenyl)-5-hydroxy-1morpholin-4-yl-pentan-1-one (230 gm, ee>99.9%).

EXAMPLE 6

Process for the preparation of 1-(4-Fluoro-phenyl)-5-hydroxy-5-morpholin-4-yl-pentan-1-one 10 gms of 1-(4-Fluoro-phenyl)-5-morpholin-4-yl-pentane-1,5-dione was taken in 62 ml of toluene to this 46 ml of (−)-Diisopinocampheyl chloroborane (DIP chloride) solution was added at 0-5° C. Stirred the reaction mass for about 6 hours and quenched the reaction mass with 750 ml of 10% NaOH. To the reaction mass was washed with brine solution. Washed the obtained organic layer with ammonium chloride solution and dried over sodium sulphate. Distilled the solvent and isolated through column chromatography to get 5.5 gms of 1-(4-Fluoro-phenyl)-5-hydroxy-5-morpholin-4-yl-pentan-1-one.

EXAMPLE 7

Process for the preparation of 5-Benzyloxy-5-(4-fluoro-phenyl)-1-morpholin-4-yl-pentan-1-one 1.8 gms of Sodium hydride was taken in 50 ml of tetrahydrofuran at 0° C., to this 5 gms of 1-(4-Fluoro-phenyl)-5-hydroxy-5-morpholin-4-yl-pentan-1-one was added under nitrogen atmosphere and maintained for about 30 minutes. To the reaction mass 3.4 gms of benzyl bromide was added at 20-25° C. and stirred for about 6 hours. Quenched the reaction mass with hydrochloric acid and stirred for about 15 minutes. Separated the layers and extracted the reaction mass with ethyl acetate. Organic layer was separated and dried over sodium sulphate. Distilled off the solvent completely and isolated the compound by adding 7 ml of toluene and 35 ml of hexane. Filtered the compound, washed with hexane and dried at 35-40° C. to get 5.6 gms of 5-Benzyloxy-5-(4-fluoro-phenyl)-1-morpholin-4-yl-pentan-1-one.

EXAMPLE 8

Process for the preparation of 5-Benzyloxy-5-(4-fluoro-phenyl)-pentanoic acid 10 gms of 5-Benzyloxy-5-(4-fluoro-phenyl)-1-morpholin-4-yl-pentan-1-one was added to 100 ml of isopropyl alcohol and 7.5 gms of potassium hydroxide. Heated the reaction mass at reflux temperature and maintain for about 36 hours and distilled off solvent completely. To the obtained oily mass 60 ml of water was added and washed with dichloromethane. Layers were separated and acidify the aqueous layer with hydrochloric acid and adjusted the pH to 2.0. The obtained aqueous layer was extracted with dichloromethane and dried the organic layer over sodium sulphate followed by concentration. 6.5 gms of 5-Benzyloxy-5-(4-fluoro-phenyl)-pentanoic acid was isolated in heptane.

EXAMPLE 9

Process for the preparation of 1-[5-Benzyloxy-5-(4-fluoro-phenyl)-pentanoyl]-5-phenyl-pyrrolidin-2-one 10 gms of 5-Benzyloxy-5-(4-fluoro-phenyl)-pentanoic acid was added to 30 ml of toluene at 20-25° C., followed by 5.6 gms of triethyl amine and 5.5 gms of Pivollyl chloride. Reaction mass was stirred for about 2 hours. To the obtained reaction mass 6.5 gms of Evan's auxiliary and 20 ml of dimethyl ammonium phosphate and 0.2 gms of dimethyl formamide were added. Heated the reaction mass at reflux temperature and maintained for about 6-8 hours. Cooled the reaction mass to 20-25° C. and 20 ml of water was added. Stirred the reaction mass and separated the organic layer and aqueous layer was extracted with toluene. Combined all organic layers and washed with brine solution. Separated the organic layer and dried over sodium sulphate and distilled the solvent completely under reduced pressure at 50-55° C. The obtained oily mass was taken in toluene and hexane was added and stirred for about 1-2 hours at 0-5° C. Filtered the compound, washed with hexane and dried at 40-45° C. to get 12 gms of 1-[5-Benzyloxy-5-(4-fluoro-phenyl)-pentanoyl]-5-phenyl-pyrrolidin-2-one.

EXAMPLE 10

Process for the preparation of 3-[5-Benzyloxy-2-[(4-benzyloxy-phenyl)-(4-fluoro-phenylamino)-methyl]-5-(4-fluoro-phenyl)-pentanoyl]-4-phenyl-oxazolidin-2-one 18 ml of Dichloromethane was added to 2.1 ml of TiCl$_4$ at 20-25° C. under nitrogen atmosphere. Cooled the reaction mass to 0° C., 2 ml of Ti(O-ipr)₄ was added and stirred for about 15 minutes. To the reaction mass 50 ml Dichloromethane, 10 gms of 1-[5-Benzyloxy-5-(4-fluoro-phenyl)-pentanoyl]-5-phenyl-pyrrolidin-2-one and 13.7 gms of Imines were added at 20-25° C. under nitrogen atmosphere. The reaction mass was cooled −30 to −35° C. and 5.8 gms of Diisopropyl ethyl amine was added. Stirred the reaction mass for about 15 minutes and TiCl₄ solution was added. Stirred the reaction mass for about 2-3 hours at −30 to −35° C. and 60 ml of isopropyl alcohol was added followed by 50 ml of Dichloromethane and stirred the reaction mass for about 60 minutes. 6% Tartaric acid solution was added to the reaction mass at 20-25° C. and stirred for about 2 hours. Separate the organic layer and extract the reaction mass with 100 ml of dichloromethane. Combined the organic layers and washed with H₂O followed by brine solution. Separated the organic layer and dried over Sodium Sulfate. Distilled the solvent completely under reducing pressure at 50-55° C. and 500 ml of methanol was added. Stirred the reaction mass for about 1-2 hours at 20-25° C., filtered the compound, washed with methanol and dried at 60-65° C. to get 8 gms of 3-[5-Benzyloxy-2-[(4-benzyloxy-phenyl)-(4-fluoro-phenylamino)-methyl]-5-(4-fluoro-phenyl)-pentanoyl]-4-phenyl-oxazolidin-2-one.

EXAMPLE 11

Process for the preparation of 5-Benzyloxy-2-[(4-benzyloxy-phenyl)-(4-fluoro-phenylamino)-methyl]-5-(4-fluoro-phenyl)-pentanoic acid methyl ester 10 gms of 3-[5-Benzyloxy-2-[(4-benzyloxy-phenyl)-(4-fluoro-phenylamino)-methyl]-5-(4-fluoro-phenyl)-pentanoyl]-4-phenyl-oxazolidin-2-one was taken in dichloromethane, to this 3.6 gms of sodium methoxide was added followed by 3.2 ml of dimethylcarbonate, and 500 ml of dichloromethane. Reaction mass was stirred for about 5-7 hours. To the reaction mass 0.1 ml of hydrochloric acid was added. Separated the layers and extract the aqueous layer with 25 ml of methylene dichloride. The organic layer was washed with water and dried over sodium sulphate. Distilled the solvent completely under reduced pressure at 50-55° C. and 85 ml of methanol was added. Stirred the reaction mass for about 1-2 hours, filtered and washed with methanol and dried at 50-55° C. to get 5 gms of 5-Benzyloxy-2-[(4-benzyloxy-phenyl)-(4-fluoro-phenylamino)-methyl]-5-(4-fluoro-phenyl)-pentanoic acid methyl ester.
Recovery of Chiral Auxiliary
The filtrate obtained from the above example was separated and solvent was distilled out completely. This was triturated with heptane to recover the pure chiral auxiliary which can be used for the preparation of Ezetimibe intermediate of formula 1-[5-Benzyloxy-5-(4-fluoro-phenyl)-pentanoyl]-5-phenyl-pyrrolidin-2-one.

EXAMPLE 12

Process for the preparation of 3-[3-Benzyloxy-3-(4-fluoro-phenyl)-propyl]-4-(4-benzyloxy-phenyl)-1-(4-fluoro-phenyl)-azetidin-2-one 10 gms of 5-Benzyloxy-2-[(4-benzyloxy-phenyl)-(4-fluoro-phenylamino)-methyl]-5-(4-fluoro-phenyl)-pentanoic acid methyl ester was dissolved in 500 ml of tetrahydrofuran and cool the reaction mass to −20 to −25° C. To the reaction mass 16 ml of 1M Lithium bis(trimethylsilyl)amide was added under nitrogen atmosphere and stirred for about 30 minutes. To the reaction mass 100 ml of 2 N hydrochloride solution was added at 20-25° C. Stirred the reaction mass by adding 150 ml of ethyl acetate and separated the organic layer. Washed the organic layer with water and dried over sodium sulphate. Distilled the solvent completely under reduced pressure at 50-55° C. to get 8.0 gms of 3-[3-Benzyloxy-3-(4-fluoro-phenyl)-propyl]-4-(4-benzyloxy-phenyl)-1-(4-fluoro-phenyl)-azetidin-2-one.

EXAMPLE 13

Process for the preparation of 3-[3-Benzyloxy-3-(4-fluoro-phenyl)-propyl]-4-(4-benzyloxy-phenyl)-1-(4-fluoro-phenyl)-azetidin-2-one 2 gms of 5-Benzyloxy-2-[(4-benzyloxy-phenyl)-(4-fluoro-phenylamino)-methyl]-5-(4-fluoro-phenyl)-pentanoic acid methyl ester was dissolved in 20 ml of toluene and stirred at room temperature for 5-20 minutes. To the reaction mass 2.39 ml of N,O-Bis-(trimethylsilyl)-acetamide was added and temperature was raised to 40-60° C. To this 0.04 gms of Tetra butyl ammonium fluoride was added and reaction was monitored by TLC. Water was added and organic fraction was distilled to get 1.5 gms of 3-[3-Benzyloxy-3-(4-fluoro-phenyl)-propyl]-4-(4-benzyloxy-phenyl)-1-(4-fluoro-phenyl)-azetidin-2-one.

EXAMPLE 14

Process for the preparation of 1-(4-Fluoro-phenyl)-3-[3-(4-fluoro-phenyl)-3-hydroxy-propyl]-4-(4-hydroxy-phenyl)-azetidin-2-one 10 gms of 3-[3-Benzyloxy-3-(4-fluoro-phenyl)-propyl]-4-(4-benzyloxy-phenyl)-1-(4-fluoro-phenyl)-azetidin-2-one was dissolved in 50 ml of methanol and 5 gms of 5% Pd/C was added at 20-25° C. Reaction mass was maintained about 30 minutes under hydrogen pressure. Filtered the catalyst and washed with methanol. The obtained reaction mass was distilled under vacuum at 70° C. and recrystalised from dichloromethane to produce 5 gms of 1-(4-Fluoro-phenyl)-3-[3-(4-fluoro-phenyl)-3-hydroxy-propyl]-4-(4-hydroxy-phenyl)-azetidin-2-one.

We claim:
1. A process for preparing (S)-5-(4-fluoro-phenyl)-5-hydroxy-1morpholin-4-yl-pentan-1-one having the formula

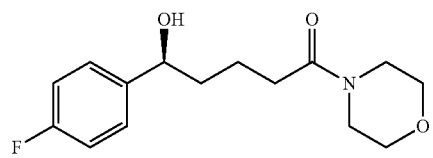 [SMILES: O=C(CCC[C@H](O)c1ccc(F)cc1)N1CCOCC1]

comprising:
resolving 5-(4-fluorophenyl)-5-hydroxy-1-morpholin-4-yl-pentane-1-one of the following formula

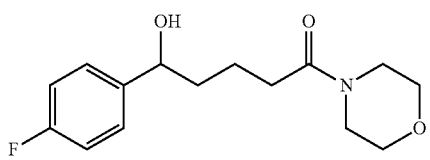 [SMILES: O=C(CCCC(O)c1ccc(F)cc1)N1CCOCC1]

using a lipase enzyme of *Candida antartica* lipase (CAL-A) in the presence of a suitable solvent and an acylating agent.

2. The process of claim 1, wherein in acylating agent is selected from the group consisting of vinyl acetate, vinyl propionate, isopropenyl acetate, succinic anhydride, and acetic anhydride.

3. A process for the preparation of Ezetimibe comprising the steps of:

a) protecting the compound formula 3 with a suitable protecting group to obtain a compound of formula 3(a)

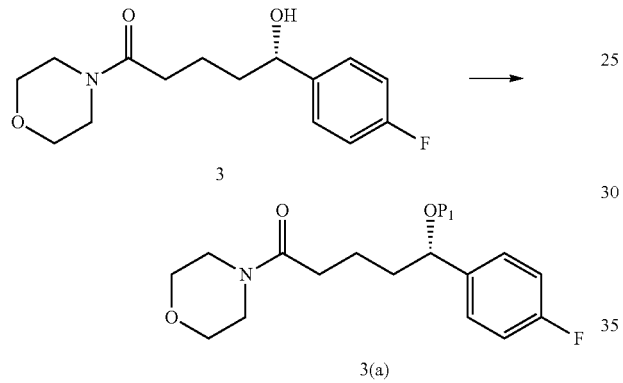

wherein $P_1$ is a hydroxyl protecting group;

b) hydrolyzing the compound of formula 3(a) to obtain a compound of formula 4;

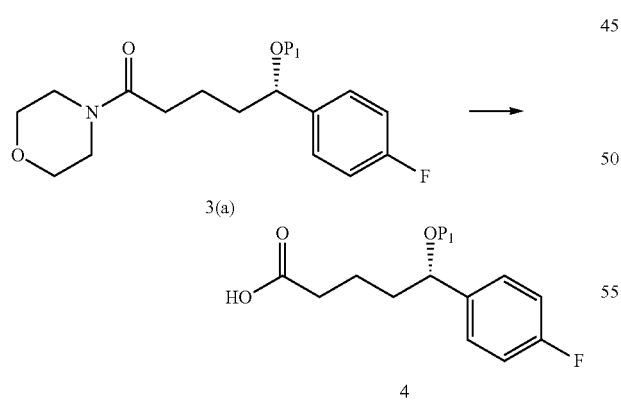

c) reacting the compound of formula 4 with pivaloyl chloride and acylating the product with a chiral auxiliary of formula 5 wherein R is $C_1$-$C_6$ alkyl, phenyl, naphthyl, substituted phenyl, substituted naphthyl, $C_1$-$C_6$ alkoxycarbonyl, or benzyl, in the presence of a base to obtain a compound of formula 6;

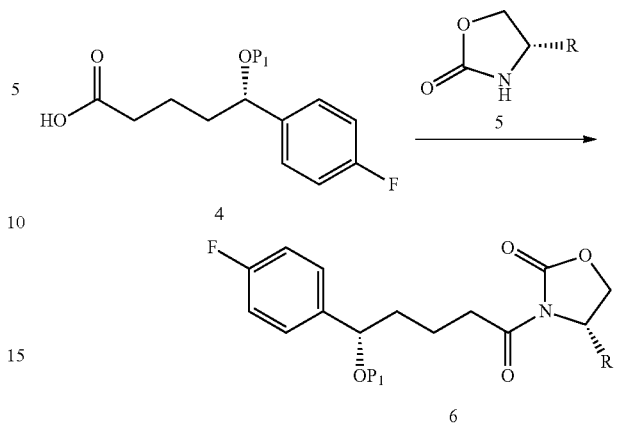

d) reacting the compound of formula 6 with a protected imine compound of formula 7 in a suitable solvent in the presence of an organic amine base and a Lewis acid to obtain a compound of formula 8

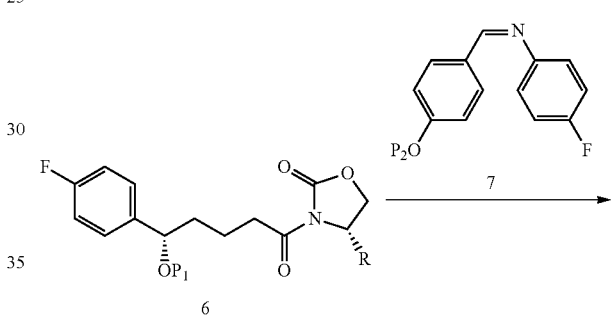

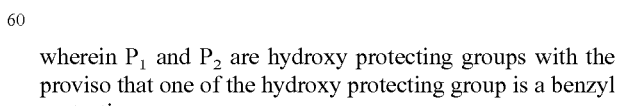

wherein $P_1$ and $P_2$ are hydroxy protecting groups with the proviso that one of the hydroxy protecting group is a benzyl protecting group;

e) reacting the compound of formula 8, with an alkalimetal alkoxide or aryloxide in a suitable solvent to obtain an alkyl or aryl ester compound of formula 9

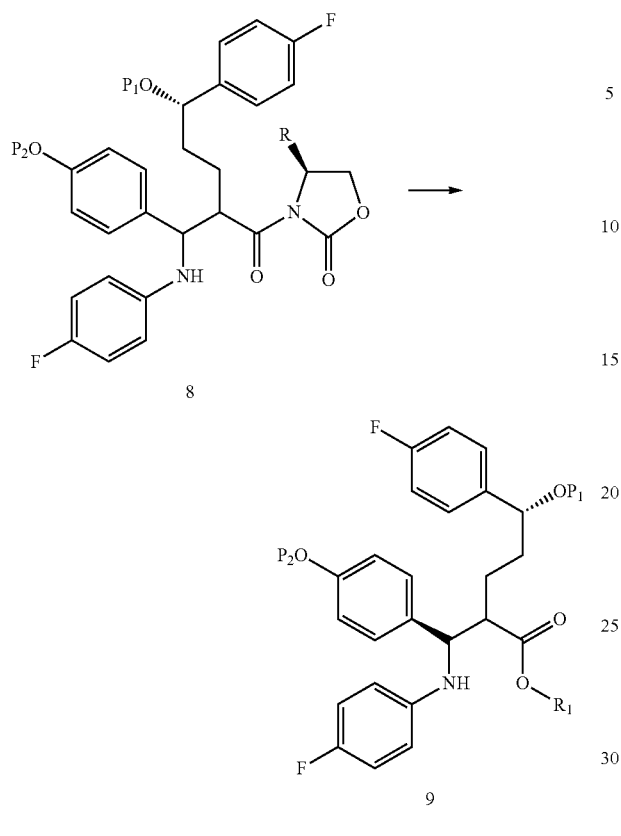

wherein $R_1$ is $C_1$-$C_6$ alkyl, substituted $C_1$-$C_6$ alkyl, aryl or substituted aryl;

f) cyclizing the compound of formula 9 in the presence of a non-nucleophilic base to obtain an azetidinone compound of formula 10;

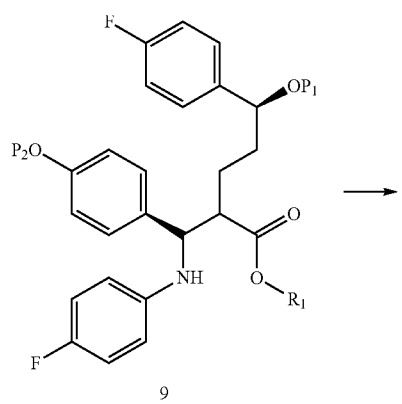

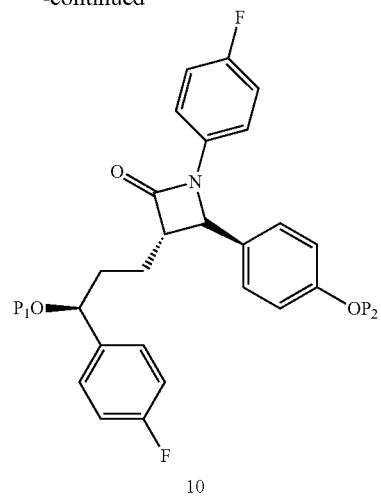

g) removing the hydroxy protecting groups; and
h) isolating the ezetimibe;

wherein the compound of formula 3 is prepared by resolving 5-(4-fluorophenyl)-5-hydroxy-1-morpholin-4-yl-pentane-1-one of the following formula

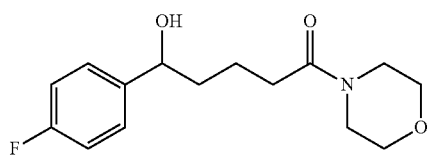 [SMILES: O=C(CCCC(O)c1ccc(F)cc1)N1CCOCC1]

using a lipase enzyme of *Candida antarctica* lipase (CAL-A) in the presence of a suitable solvent and an acylating agent.

4. The process according to claim 3, wherein in step (a), the hydroxy protecting group is a benzyl or silyl protecting group.

5. The process according to claim 3, wherein in step (c), the chiral auxiliary is (4S)-4- phenyl-2-oxazolidinone.

6. The process according to claim 3, wherein in step (d), the solvent is dichloromethane.

7. The process according to claim 3, wherein in step (d), the organic amine base is N,N-diisopropylethylamine and the Lewis acid is $TiCl_4$.

8. The process according to claim 3, wherein in step (e), the alkalimetal alkoxide is sodium methoxide.

9. The process according to claim 3, wherein in step (e), the solvent is dichloromethane.

10. The process according to claim 3, wherein in step (f), the non-nucleophilic base is lithium bis(trimethylsilyl) amide or bistrimethyl acetamide.

11. The process of claim 1 further comprising the step of converting the (S)-5-(4-fluoro-phenyl)-5-hydroxy-1-morpholin-4-pentan-1-one to Ezetimibe.

* * * * *